United States Patent [19]

Okonogi et al.

[11] Patent Number: 5,334,723
[45] Date of Patent: Aug. 2, 1994

[54] 2-PIPERIDINECARBOXYLIC ACID DERIVATIVE, ONCOGENE SUPPRESSOR AND AGENT FOR OBTAINING REVERTANTS

[75] Inventors: Tsuneo Okonogi; Osamu Makabe; Yuichi Yamamoto; Osamu Itoh; Tsutomu Tsuruoka; Takayuki Usui; Seiji Shibahara; Kozo Nagaoka; Shigeharu Inouye, all of Kanagawa; Nobuko Okada, Tokyo; Susumu Nishimura, Chiba, all of Japan

[73] Assignee: Meiji Seika Kaisha, Ltd., Tokyo, Japan

[21] Appl. No.: 937,112

[22] Filed: Aug. 31, 1992

[30] Foreign Application Priority Data

Aug. 29, 1991 [JP] Japan .................................. 3-219022
Sep. 9, 1991 [JP] Japan .................................. 3-229190

[51] Int. Cl.⁵ .................. C07D 211/76; C07D 211/86; C07D 211/88
[52] U.S. Cl. ...................................... 546/298; 546/297
[58] Field of Search ............................... 546/298, 297

[56] References Cited

PUBLICATIONS

J. E. Baldwin et al., Tetrahedron Letters, 28 (31), 3605–3608 (1987).
J. K. Still, Tetrahedron Letters, 24 (41), 4405–4408 (1983).
R. K. Boeckman, Jr., Journal of American Chemical Society, 111, 8036–8037 (1989).
R. S. Garigipati, Tetrahedron Letters, 31 (14), 1969–1973 (1990).

*Primary Examiner*—Alan L. Rotman
*Attorney, Agent, or Firm*—Sughrue, Mion, Zinn, Macpeak & Seas

[57] ABSTRACT

A novel 2-piperidinecarboxylic acid derivative represented by the formula:

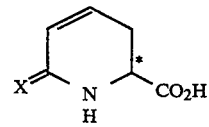

wherein X represents an oxygen atom, a sulfur atom or a nitrogen atom to which a hydrogen atom is bound; and * represents that the configuration of the carbon atom binding to the carboxyl group is (S), (R) or a mixture of (S) and (R); and a pharmaceutically acceptable salt thereof which exerts an antitumor effect over a wide range of tumor cells.

7 Claims, 2 Drawing Sheets

2-PIPERIDINECARBOXYLIC ACID DERIVATIVE, ONCOGENE SUPPRESSOR AND AGENT FOR OBTAINING REVERTANTS

FIELD OF THE INVENTION

This invention relates to a novel 2-piperidinecarboxylic acid derivative having a wide antitumor-spectrum and showing a revertant-inducing effect.

BACKGROUND OF THE INVENTION

In recent years, there is the highest mortality rate from malignant tumors mainly comprising cancers in various countries and, therefore, it has been urgently required to establish effective therapeutics therefor. The known methods for treating malignant tumors include surgical extraction, radiotherapeutics, and subsequent maintenance therapeutics with the use of antibiotics, vegetable alkaloids or synthetic anticancer drugs. However, no satisfactory treatment has been established for, in particular, solid cancer.

The present inventors previously found that an antifungal microbial metabolite SF2698 as described in EP-A-458259 has an antitumor activity (Proceedings of 50th General Meeting of Japan Society of Cancer, page 2065, 1991).

With the progress in studies on cancer genes, a number of oncogenes have been found in human cancers. Among these oncogenes, ras gene is activated through one point mutation in various human cancers in, for example, pancreas, intestinum crassum, lung, stomach and skin, though healthy subjects carry this ras gene in a normal state. Accordingly, it is considered that the ras gene might relate to canceration in human and the malignancy of cancers. In order to find a novel carcinostatic substance, the present inventors screened various compounds by assaying the inhibitory effect on the growth of mouse NIH3T3 cells which had been transformed with activated c-Ha-ras gene isolated from a tumor of a human patient with melanoma. As a result, it was found that L-$\beta$-(5-hydroxy-2-pyridyl)alanine (azatyrosine) selectively inhibited the growth of NIH3T3 cells transformed with the activated ras gene at a concentration of 500 μg/ml but never inhibited the growth of normal NIH3T3 cells at the same concentration. It was further found that cells surviving after treatment with azatyrosine were revertant cells (JP-A-1-110627, the term "JP-A" as used herein means an "unexamined Japanese patent application").

SUMMARY OF THE INVENTION

An object of the present invention is to provide a novel compound effective for various tumors. The present inventors have conducted extensive studies on finding compounds having an antitumor activity among various microbial metabolites and synthetic compounds, and as a result, it was found that a 2-piperidinecarboxylic acid derivative has an excellent antitumor activity over a wide range. Further, the present inventors have attempted to detect a substance which inhibits the growth of the NIH3T3 cells transformed with the ras gene at a lower concentration, and as a result, it was found that a 2-piperidinecarboxylic acid derivative has exerts an oncogene supressing effect and revertant-inducing effect at a lower concentration, similar to that of azatyrosine.

The present invention provides a compound represented by formula (I):

wherein X represents an oxygen atom, a sulfur atom or a nitrogen atom to which a hydrogen atom is bound; and a pharmaceutically acceptable salt thereof.

BRIEF DESCRIPTION OF THE DRAWINGS

In FIGS. 1(a) and 1(b) □—is a line for control and—·—for the case of adding the compound of the invention (40 μg/ml).

In FIG. 2, lane 1 is a electrophoretic pattern for normal NIH3T3 cells, lane 2 for revertants and lane 3 for NIH3T3 cells transformed with the activated ras gene.

DETAILED DESCRIPTION OF THE INVENTION

In formula (I), the configuration of the carbon atom binding to the carboxyl group may be (S), (R) or a mixture of (S) and (R). When X is an oxygen atom or a sulfur atom, said hydrogen atom is bound, said pharmaceutically acceptable salt may be selected from, for example, hydrochloride, bromate, citrate or oxalate.

In a typical case, the compounds represented by formula (I) according to the present invention may be produced by, for example, methods shown by the following reaction schemes 1 to 3. The carbon atom binding to the carboxyl group is hereinafter referred to as "*" for short.

A compound of the present invention represented by formula (I), wherein X is an oxygen atom, is produced by the following reaction scheme 1.

-continued
Reaction Scheme 1

(wherein X is an oxygen atom and * is (S))

First, an amino group and a carboxyl group of L-homoserine, which is a starting material, are successively protected in accordance with a conventional method employed in the field of amino acid chemistry. Preferred as the amino-protecting group are those which may be deprotected under mild conditions, such as benzyloxycarbonyl group or a t-butyloxycarbonyl group. The carboxyl group may be protected by a common alkyl ester protection to thereby form, for example, methyl ester or ethyl ester.

As the reaction scheme shows, a preferable example of this reaction proceeds as follows. Namely, the starting L-homoserine is treated with di-t-butyl dicarbonate to protect the amino group with a t-butoxycarbonyl group (Boc). Then it is treated with dimethylsulfuric acid to convert the carboxyl group into methyl ester. In the next step, the primary hydroxyl group of the protected L-homoserine thus obtained is oxidized to obtain aldehyde compound 2. The oxidation may be effected with the use of various chromic acids or chromium derivatives. Alternatively, it may be performed by Pfitzner-Moffatt oxidation using dimethylsulfoxide and dicyclohexyl carbodiimide or Swern oxidation using dimethylsulfoxide and oxalyl chloride. Further, the compound 2 may be prepared by a method reported by J. E. Baldwin et al. [Tetrahedron Letters, 28 (31), 3605–3608 (1987)].

Subsequently, the compound 2 is subjected to a conventional reaction for forming an unsaturated bond by using phosphorus ylide. Wittig reaction or Horner-Emmons reaction may be suitably selected therefor. As the reaction scheme shows, the compound 2 is reacted with t-butyltriphenylphosphoranylideneacetate to thereby give olefin compound 3. In general, an unsaturated bond formed by, for example, Wittig reaction is obtained as a mixture of cis- and trans-forms. A method for selectively producing cis-compound alone as described below enables an effecient production of the compound 3. The olefin compound 3 is then subjected to Michael addition by using various mercaptans or selenium compounds. Preferable examples of the mercaptans include phenylmercaptan and benzylmercaptan. As shown in the reaction scheme, phenylmercaptan is added in the presence of an organic base and the resulting mixture is heated to 50° to 100° C. for several hours to obtain compound 4.

Without purifying the compound 4 thus obtained, the t-butyl ester group and the Boc group thereof are deprotected, and then, it is cyclized. That is, after the compound 4 is deprotected by treating with aqueous trifluoroacetic acid, the deprotected compound is neutralized and concentrated so that dehydration and cyclization can easily proceed. Thus, cyclic compound 5 is obtained. The compound 5 is converted into dihydro 2-pyridone compound 6 through oxidation and elimination. Preferred as the oxidizing agent to be used therefor are mild ones capable of oxidizing sulfides into sulfoxides. Examples thereof include iodine, periodic acid, aqueous solution of hydrogen peroxide and peracetic acid. When the compound 5 is treated with, for example, peracetic acid, a sulfoxide intermediate may be quantitatively obtained. The elimination reaction of this sulfoxide may be performed by heating in a high-boiling point solvent such as toluene or xylene. For example, the sulfoxide intermediate is dissolved in xylene and heated to 140° C. for 1 hour. Thus compound 6 is obtained. Then the methyl ester group of the compound 6 is hydrolyzed. As a result, the compound of the present invention represented by formula (I) wherein X is an oxygen atom is obtained. The hydrolysis may be performed by a conventional method with the use of an acid or an alkali. Alkali hydrolysis with the use of caustic soda is preferable therefor.

One of the structural characteristics of the compound of the present invention represented by formula (I) resides in the cis-olefin on the piperidine ring. In the above-mentioned production method, the cis/trans-olefin mixture (compound 3) is successively subjected to Michael addition, cyclization and elimination to thereby give the cis-olefin. More efficiently, the cis-olefin is selectively synthesized from the above-mentioned intermediate 2. The selective synthesis of the cis-olefin is reported by J. K. Still [Tetrahedron Letters, 24 (41), 4405–4408 (1983)]. Further, R. K. Boeckmann Jr. reported allyl bistrifluoroethylphosphonoacetate (compound 7) [Journal of American Chemical Society, 111, 8036–8037 (1989)].

The compound 7 described in the literature as cited above and the compound 2 are subjected to Horner-Emmons reaction and thus compound 8 is obtained at a yield of 65%. The allyl protecting group of the compound 8 is deprotected in a conventional manner by treating with tetrakistriphenylphosphine palladium in an organic solvent in the presence of 2-ethylhexanoic acid potassium salt. Thus free acid compound 9 is obtained. The cyclization of the compound 9 into the compound 6 may be performed in the same manner as the cyclization of the compound 4 to the compound 5. Namely, the compound 9 is treated with hydrated trifluoroacetic acid and the free amino acid intermediate thus obtained is dehydrated and condensed. Thus the compound 6 is obtained almost quantitatively.

The compound of the present invention represented by formula (I) wherein X is a sulfur atom may be produced by the method shown by the following reaction scheme 2.

Reaction Scheme 2

(wherein X is a sulfur atom and * is (S))

First, the oxygen atom in the amidocarbonyl group of the above-mentioned compound 6 is converted into a sulfur atom. This conversion may be performed by heating the compound 6 with phosphorus pentasulfide or Lawesson's reagent, 2,4-bis(4-methoxyphenyl)-1,3-dithia-2,4-diphosphetan-2,4-disulfide in an inert organic solvent. For example, the compound 10 may be easily obtained by heating the compound 6 with phosphorus pentasulfide in toluene at 60° C. for 1 hour. Next, the methyl ester of the compound 10 is hydrolyzed to thereby give the compound represented by formula (I) wherein X is a sulfur atom. The compound 10 may be hydrolyzed in the same manner as the compound 6 to give the compound of formula (I) wherein X is an oxygen atom. Namely, alkali hydrolysis with the use of caustic soda is suitable therefor.

The compound represented by formula (I) wherein X is a nitrogen atom to which a hydrogen atom is bound while the configuration of * is (S), is the above-mentioned substance SF2698 obtained by incubating an Actinomycete strain SF2698. However, compounds, wherein * is (R) or a mixture of (R) and (S), are novel ones -which cannot be obtained by cultivation of said microorganisms. These novel substances may be produced by a synthetic method shown by the following reaction scheme 3 developed by the present inventors. A method for producing an (R), (S) mixture will be illustrated hereinbelow by way of example.

Reaction Scheme 3

1) (Boc)$_2$O
2) (CH$_3$)$_2$SO$_4$
3) CrO$_3$/Py
$\xrightarrow{90\%}$

-continued
Reaction Scheme 3

(wherein X is a nitrogen atom to which a hydrogen

-continued
Reaction Scheme 3 atom is bound; and * is an (R), (S) mixture)

The starting material 1 and the intermediates 2, 8 and 9 are each shown in the above reaction schemes 1 and 2 and the configuration therein represented by * is an (R), (S) mixture. Thus these compounds are optically inactive. These intermediates may be prepared by the same synthetic procedures as described above using DL-homoserine as a starting material. From the compound 9, the compound represented by formula (I), wherein X is a nitrogen atom to which a hydrogen atom is bound, may be synthesized by synthesizing a compound having a nitrile group and a free amino group as an intermediate and then subjecting this intermediate to the cyclic amidine synthesis. The cyclic amidine compound may be synthesized by the method reported by R. S. Garigipatai [Tetrahedron Letters, 31 (14), 1969–1972 (1990)].

After activating the free carboxyl group of the compound 9, the resulting compound is treated with amonia to thereby give an amide intermediate. The activation of the carboxyl group may be performed by a known method such as the acid chloride method or the mixed acid anhydride method, with the latter being preferred. For example, said compound is treated with butyl chlorocarbonate to give an acid anhydride and then treated with aqueous ammonia to give an amide intermediate. This amide intermediate is dehydrated and thus nitrile compound 11 is obtained. The amide compound may be dehydrated in a conventional manner. For example, the dehydration may be performed by adding tosyl chloride in the presence of pyridine and heating. Thus compound 11 is obtained. Then the amino protecting group, i.e., t-butyloxycarbonyl group (Boc) of the compound 11 is eliminated by treating with hydrochloric acid. Thus the desired intermediate 12 having a nitrile group and a free amino group is obtained. This compound 12 is stirred in an organic solvent in the presence of trimethylammonium at room temperature in accordance with the method of Garigipatai. After the completion of the reaction, the excessive trimethylammonium is decomposed with hydrochloric acid and thus a cyclic amidine intermediate 13 is obtained. The ester protecting group of the compound 13 is eliminated by hydrolyzing with hydrochloric acid and purified to thereby give the target compound of the present invention represented by formula (I) wherein X is a nitrogen atom to which a hydrogen atom is bound and * is an (R), (S) mixture.

The method for preparing the intermediate 9 wherein * is (S) has been illustrated in the above reaction scheme 1. The compound represented by formula (I) wherein * is (S), namely, the substance SF2698, is obtained by subjecting the intermediate 9 to cyclic amidine synthesis. The present invention further provides a method of chemically producing the substance SF2698 as the following Examples show.

The compound represented by formula (I) can effectively inhibit the growth of cells transformed with an oncogene vitro and convert the surviving cells into revertants. When administered to a nude mouse, the revertants obtained by the treatment with this compound shows little carcinogenesis, though it produces the activated ras gene product similar to the revertants obtained by treating with azatyrosine. From a morphological viewpoint, the revertants are flat and thus closely similar to normal cells. They can be subcultured.

When the compound of the present invention is used as an antitumor agent or an oncogene suppressor, it may be parenterally or orally administered. In the case of the parenteral administration, it may be formulated into a solution or a suspension for intravenous or intramuscular injection. The dose thereof for mammals including human ranges from 10 to 400 mg/kg body weight/day, preferably from 10 to 200 mg/kg body weight/day. In the case of the oral administration, it may be mixed with, for example, pharmaceutically acceptable carriers and encapsulated in gelatin capsules, if desired. Alternatively, it may be mixed with other medicines, starch, lubricants and other pharmaceutically acceptable excipients, if desired, and then formulated into tablets each containing from 20 mg to 200 mg of the active ingredient.

The antitumor effects of the compounds of the present invention is illustrated in the following Test Examples.

TEST EXAMPLE 1

Antitumor effect on various mouse tumor cells

The effects of the compounds of the present invention were evaluated by using various mouse tumor cell strains shown in Table 1 which could be subcultured and evidently induced the formation of tumors when transplanted into mice. The P388 and L1210 cells are derived from mouse leukemia. The MethA cells, the 3LL cells and the B16 cells are derived from solid cancer, Lewis lung cancer and melanoma, respectively.

The cells subcultured in a $CO_2$ incubator were each suspended in an RPM1 medium or Dulbecco's modified MEM medium, supplemented with 10%(v/v) fetal serum so as to give a cell density of $5 \times 10^4$ cells/mi. To a 135 $\mu$l portion of the suspension was added each test compound shown in Table 1 followed by 3-day incubation in a $CO_2$ incubator. After the incubation was completed, 50% inhibition concentration ($IC_{50}$) was determined by the MTT assay (Igaku no Ayumi, 128, 733 (1984)). The results are shown in Table 1.

TABLE 1

| Compound | $IC_{50}$ ($\mu$g/ml) | | | | |
|---|---|---|---|---|---|
| | P388 | L1210 | MethA | 3LL | B16 |
| Compound of Ex. 3 | 5.0 | 9.0 | 11.0 | 11.0 | 45 |
| SF2698 | 120 | 65 | 46 | 51 | 41 |
| Compound of Ex. 1 | 200 | 130 | 100 | 100 | 90 |

TEST EXAMPLE 2

Antitumor effects on various human tumor cells

The antitumor effects of the compounds of the present invention were evaluated in the same manner as in Test Example 1 except that various human tumor cells were employed. The HL60 cells, the CCRF-CCM cells and the QG5 cells are derived from human leukemia, human T cells and human lung cancer, respectively.

TABLE 2

| Compound | $IC_{50}$ ($\mu$g/ml) | | |
|---|---|---|---|
| | HL60 | CCRFCEM | OG56 |
| Compound of Ex. 3 | 20 | 20 | 70 |
| SF2698 | 45 | 45 | 80 |
| Compound of Ex. 1 | 90 | 90 | 180 |

TEST EXAMPLE 3

Acute toxicity of the compounds of the invention

The compounds of the present invention were intravenously administered to male BDF mice in order to examine the acute toxicity (each group having 3 mice). Table 3 shows the doses causing no death.

TABLE 3

| Compound | Survival dose (mg/kg) |
|---|---|
| Compound of Ex. 1 | 1000 |
| SF2698 | 300 |
| Compound of Ex. 3 | 800 |
| Compound of Ex. 4 | 600 |

The following Examples are given to further illustrate the present invention but are not to be construed to limit the scope of the invention.

EXAMPLE 1

The compounds of the present invention represented by formula (I) wherein X is an oxygen atom and * is (S) may be produced in the following manner in accordance with the above-mentioned reaction scheme 1.

10.4 g (87 mmol) of L-homoserine and 7.34 g of $NaHCO_3$ were dissolved in 50 ml of H20 and 75 ml of dioxane. After adding 21 g of di-t-butyl dicarbonate ($Boc_2O$), the mixture was stirred at room temperature for 16 hours. Then the reaction mixture was completely concentrated to dryness and the residue was pulverized with ether. The resulting powder was dissolved in 60 ml of dimethylformamide (DMF) and 12.3 ml of dimethylsulfuric acid was added under ice-cooling. Then the mixture was stirred at the same temperature for 2 hours. The reaction mixture was added to a mixture of 100 ml of ice-cooled aqueous solution of sodium chloride and 100 ml of ethyl acetate and extracted with ethyl acetate thrice. The organic layers were combined and washed with saturated aqueous solution of sodium chloride. After drying over $MgSO_4$ and concentrating under reduced pressure, N-Boc-L-homoserine was obtained.

70.4 ml of pyridine was added to 700 ml of dichloromethane and the mixture was ice-cooled. Then 43.5 g of $CrO_3$ was added thereto and the resulting mixture was allowed to react at the same temperature for 1 hour. Then the N-Boc-L-homoserine obtained above, dissolved in 300 ml of dichloromethane, was added thereto, followed by stirring for 15 minutes. After separating the supernatant, the residue was washed with dichloromethane. The organic layers were combined and 300 ml of ice-cooled water was added thereto. Then the pH value thereof was adjusted to 2.0 with 6N HCl. The organic layer was collected, washed with aqueous solution of sodium chloride and concentrated under reduced pressure. The oily residue was purified by column chromatography with the use of 300 g of Wako Gel C-300 and the target compound eluted with toluene/ethyl acetate (5:1 by volume) was collected. After concentrating the eluate, 19 g of the compound 2 (aidehyde) was obtained.

3.8 g of the compound 2 was dissolved in 60 ml of chloroform and 6.4 g of $Ph_3P=CHCO_2t$—Bu was added thereto. After stirring at room temperature for 16 hours, the reaction mixture was concentrated under reduced pressure and the residue was purified with a column of 70 g of Wako Gel C-300. All of the fractions containing cis- and trans-compounds eluted with ethyl acetate/n-hexane (2:5 by volume) were collected and concentrated. After crystallizing from petroleum ether, 2.6 g of the compound 3 was obtained in the form of a cis/trans olefin mixture.

Compound 3 (trans-form): NMR (CDCl$_3$) δppm: 1.41 (9H, s, t-Bu), 1.44 (9H, s, t-Bu), 2.52 and 2.63 (2H, m, —CH$_2$—), 3.72 (3H, s, —CH$_3$), 4.41 (1H, m, —CH—CO$_2$), 5.01 (1H, broad, d, —NH—), 5.76 (1H, dt, J=15.82, 1.32 Hz, =CHCO), 6.68 (1H, dt, J=15.82, 7.47 Hz, —CH=CH—CO). 1.65 g (5 mmol) of the olefin mixture was dissolved in 15 ml of DMF and 1.54 ml of thiophenol and 0.5 ml of piperidine were added thereto. The reaction mixture was allowed to react at 60° C. for 2 hours, cooled and diluted with ethyl acetate. Then it was washed with aqueous solution of sodium chloride to thereby eliminate the DMF and the organic layer was concentrated under reduced pressure to thereby give the compound 4.

Compound 4 (diastereomer mixture): NMR (CDCl$_3$) δppm: 1.40 (18H, s, t-Bu), 1.70-2.15 (2H, m, —CH$_2$—), 2.30-2.72 (2H, m, —CH$_2$—), 3.20-3.55 (1H, m, —CHSPh—), 3.71 (3H, s, CH$_3$), 4.30-4.80 (1H, m, —CHCO$_2$—), 4.90-4.15 (1H, broad d, —NH—), 7.15-7.60 (5H, m, Ph).

To the residue, 20 ml of 90% trifluoroacetic acid (TFA) (10%: water) was added and the mixture was stirred at room temperature for 2 hours. Then the reaction mixture was concentrated under reduced pressure, diluted with water and washed with benzene to thereby remove the excessive thiophenol. The aqueous layer was concentrated to dryness and the residue was dissolved in water and neutralized with triethylamine to the pH value of 4.5. Next, it was concentrated under reduced pressure and then subjected to azeotropy with benzene for dehydration. The residue was dissolved in methylene chloride, successively washed with diluted hydrochloric acid and an NaHCO$_3$ solution and dried over magnesium sulfate. The organic layer was concentrated under reduced pressure and the residue was crystallized from ethyl acetate/hexane to thereby give 1.1 g of the target cyclic compound 5.

Compound 5 (diastereomer mixture): NMR (CDCl$_3$) δppm: 2.08-2.87 (4H, m, —CH$_2$—CHPh—CH$_2$—), 3.31-3.70 (1H, m, —CH—), 3.76 (3H, s, CH$_3$), 3.96-4.41 (1H, m, —CHCO$_2$—), 6.37 (1H, broad s, —NH—), 7.22-7.60 (5H, m, Ph).

The cyclic compound 5 was dissolved in 15 ml of methylene chloride and 890 mg of 40% AcO$_2$H was added dropwise thereto. Then the reaction mixture was washed with an aqueous solution of NaHCO$_3$, water and a 1% aqueous solution of NaHSO$_3$ and dried over MgSO$_4$. The solution was concentrated under reduced pressure and thus a sulfoxide intermediate was obtained. This sulfoxide intermediate was dissolved in xylene (40 ml) and heated to 140° C. for 1 hour. The reaction mixture was concentrated under reduced pressure and the residue was purified by column chromatography with the use of 70 g of Wako Gel C-300. After eluting with chloroform/methanol (20:1 by volume), 600 mg of the cyclic compound 6 was obtained.

Compound 6: NMR (CDCl$_3$) δppm: 2.70 (2H, m, —CH$_2$—), 3.79 (3H, s, CH$_3$), 4.22 (1H, ddd, J=8.57, 6.81, 1,97 Hz, —CHCO$_2$—), 5.90 (1H, dq, J=9.89, 1.97 Hz, =CHCO—), 6.17 (1H, broad s, —NH—), 6.56 (1H, dt, J=9.89, 4.12 Hz, —CH=CHCO—).

IR (KBr) νcm$^{-1}$; 1742, 1681, 1603.

[α]$^{25}_D$= −135° (C 1.57, CHCl$_3$).

m.p.: 80°-82° C.

200 mg of the compound 6 was dissolved in 2 ml of tetrahydrofuran (THF) and 2.8 ml of NaOH was added thereto under ice-cooling. After reacting for 10 minutes, the reaction mixture was diluted with ethyl acetate and ice-cooled water and adjusted to pH 2.0 with 6N HCl for extraction. The organic layer was washed with aqueous solution of sodium chloride, dried over MgSO$_4$ and then concentrated to dryness to thereby give an oily residue. This oily residue was pulverized with hexane. The residue was dissolved in 4 ml of chlroform and neutralized with NaHCO$_3$. Then it was purified by column chromatography with the use of 100 ml of Diaion HP20 (Mitsubishi Kasei Corporation) and eluted with water. Fractions containing the target compound were concentrated and thus 120 mg of the compound of formula (I) wherein X was an oxygen atom and * was (S) was obtained.

Compound of Example 1 [the compound of formula (I) wherein X is an oxygen atom and * is (S)]:

NMR (D$_2$O) δppm: 2.59 and 2.73 (2H, m, —CH$_2$—), 4.08 (1H, dd, J=7.77, 7.22 Hz, —CHCO—), 5.85 (1H, dt, J=9.99, 1.94 Hz, =CH—CO), 6.77 (1H, dt, J=9.99, 4.16 Hz, —CH=CH—CO) .

[α]$^{25}_D$= −54° (C 1.0, H$_2$O).

EXAMPLE 2

The cyclic compound 6 produced in Example 1 may be obtained more efficiently by the following method.

1.52 g of lithium bromide was dissolved in 40 ml of dry THF and 7 g of bis-trifluoroethyl phosphonate (the compound 7) was added thereto, followed by stirring at room temperature for 10 minutes. Then 2.4 ml of triethylamine was added and the resulting mixture was cooled to −20° C. 3.46 g of the aldehyde compound 2 was dissolved in a small amount of dry THF and added thereto and the mixture was stirred at −20° to −10° C. for 3 hours. Next, 100 ml of ethyl acetate and 100 ml of aqueous solution of sodium chloride were added to the reaction mixture and extracted under stirring. The organic layer was washed with aqueous solution of sodium chloride and dried over MgSO$_4$ and then the solvent was distilled off under reduced pressure. The residue was purified by column chromatography with the use of 260 g of Wako Gel C-300. The cis-compound eluted with ethyl acetate/n-hexane (2:5 by volume) was combined and the solvent was distilled off under reduced pressure. Thus 8.30 g of the target cis-compound was obtained.

Compound 8: NMR (CDCl$_3$) δppm: 1.42 (9H, s, t-Bu), 3.04 (2H, dt, J=7.03, 1.10 Hz, —CH=CH—CH$_2$—), 3.68 (3H, s, CH$_3$), 4.34 (1H, m, —CHCO$_2$), 4.58 (2H, m, —CO$_2$CH$_2$—), 5.10-5.40 (3H, m, —NH— and —OCH$_2$CH=CH$_2$), 5.85 (1H, m, —OCH$_2$CH=CH$_2$), 5.88 (1H, dt, J=11.65, 1.10 Hz, —CH=CHCO$_2$—), 6.19 (1H, ddd, J=11.65, 7.03, 6.81 Hz, —CH=CHCO$_2$—).

IR (CHCl$_3$) νcm$^{-1}$; 1710, 1645, 1420.

[α]$^{25}_D$= +46.6° (C 1.55, CHCl$_3$).

3.0 g of the compound 8 was dissolved in 30 ml of methylene chloride and 3.3 ml of a 1.75 M solution of 2-ethylhexanoic acid potassium salt in ethyl acetate was added thereto. Then 13 mg of tetrakistriphenylphosphine palladium [Pd(PPh$_3$)$_4$] was added thereto and the mixture was allowed to react at room temperature for 3 hours. The reaction mixture was diluted and extracted with ethyl acetate/ice-cooled water. The aqueous layer was adjusted to pH 2.0 with 6N HCl and extracted with ethyl acetate, followed by drying over MgSO$_4$. After distilling off the solvent under reduced pressure, the crude crystals thus obtained were recrystallized from ethyl acetate/n-hexane. Thus 2.3 g of the cis-olefin free carboxylic acid (the compound 9) was obtained.

Compound 9: NMR (CDCl$_3$) δppm: 1.42 (9H, s, t-Bu), 3.10 (2H, broad t, —CH$_2$—), 3.71 (3H, s, CH$_3$), 4.38 (2H, broad q, —CHCO$_2$—), 5.22 (1H, broad s, —NH—), 5.91 (1H, dt, J=11.43, 1.38 Hz, =CH—CO$_2$—), 6.30 (1H, dt, J=11.43, 7.25, —CH=CH—CO$_2$—).

IR (KBr) νcm$^{-1}$; 1759, 1684, 1645.

$[α]^{25}_D$= +60.5° (C 1.70, CHCl$_3$).

m.p.: 77°-79° C.

The compound 9 was dissolved in 30 ml of TFA and reacted at 0° C. for 2 hours. The reaction mixture was distilled off under reduced pressure and water was added thereto. Then the pH value was adjusted to 4 to 5 with triethylamine under ice-cooling and then the mixture was concentrated again. The residue was subjected to azeotropy with benzene for dehydration and thus the target compound 6 was quantitatively obtained.

EXAMPLE 3

The compound of the present invention represented by formula (I) wherein X is a sulfur atom and * is (S) may be produced by the following method.

600 mg of the cyclic compound 6 produced in Example 1 was dissolved in 10 ml of benzene. After adding 1.1 g of P$_2$S$_5$, the mixture was heated to 60° C. for 1 hour. After cooling to room temperature, the supernatant was separated and the residue was washed with benzene. The organic layers were combined and concentrated under reduced pressure. Then the residue was dissolved in methylene chloride and dried over MgSO$_4$. The solvent was distilled off under reduced pressure and the residue was then purified by column chromatography with the use of 40 g of Wako Gel C-300 and a solvent system comprising benzene/ethyl acetate (4 : 1 by volume). Fractions containing the target compound were concentrated under reduced pressure and thus 200 mg of the thioamide cyclic compound 10 was obtained.

Compound 10: NMR (CDCl$_3$) δppm: 2.56 (1H, m, —CH$_2$—), 2.73 (1H, m, —CH$_2$—), 3.83 (3H, s, CH$_3$), 4.24 (1H, ddd, J=11.54, 6.41, 2.05 Hz, —CHCO$_2$—), 6.35 (1H, ddd, J=9.74, 5.38, 3,33 Hz, =CHS—), 6.45 (1H, ddd, J=9.74, 3.08, 2.31 Hz, —CH=CHCS—).

200 mg of the compound 10 was dissolved in 2 ml of THF and 2.8 ml of 0.5N NaOH was added thereto under ice-cooling, followed by hydrolyzing at the same temperature for 10 minutes. The reaction mixture was then diluted with 10 ml of ethyl acetate and 10 ml of ice-cooled water and adjusted to pH 2.0 with 6N HCl. After extracting under stirring, the organic layer was washed with aqueous solution of sodium chloride, dried over MgSO$_4$ and treated with decoloring carbon. Then the solvent was distilled off under reduced pressure and the oily residue thus obtained was dissolved in 4 ml of water with the use of an eqivalent amount of NaHCO$_3$. Then it was purified by column chromatography with the use of Diaion HP-20 (Mitsubishi Kasei Corporaiton) to thereby give the compound represented by formula (I) wherein X was a sulfur atom and * was (S).

Compound of Example 3 [the compound of formula (I) wherein X is a sulfur atom and * is (S)]: NMR (D$_2$O) δppm: 2.61 (1H, m, —CH$_2$—), 2.71 (1H, m, —CH$_2$—), 4.09 (1H, t, J=7.82 Hz, —CHCO$_2$—), 6.31 (1H, dt, J=9.49, 1.80 Hz, —CH=CHCS), 6.51 (1H, dt, J=9.49, 4.36 Hz, —CH=CHCS).

$[α]^{25}_D$= —42.3° (C 1.50, H$_2$O).

EXAMPLE 4

The compound of the present invention represented by formula (I) wherein X is a nitrogen atom to which a hydrogen atom is bound while * is an (R), (S) mixture may be produced in the following manner.

The compound 9 wherein * was an (R), (S) mixture was obtained in the same manner as in Examples 1 and 3 except for using DL-homoserine as a starting material.

1.5 g of this compound 9 was dissolved in 15 ml of methylene chloride. 0.73 ml of N-methylmorpholine was added thereto and the mixture was cooled to —25° C. 0.86 ml of isobutylchloroformate was further added thereto, followed by stirring at —25° to —20° C. for 30 minutes. Next, 80 ml of ice-cooled 0.7N aqueous amonia was added under vigorously stirring and the mixture was allowed to react for 15 minutes. After separating the organic layer, the aqueous layer was extracted with methylene chloride and the organic layers were combined together. After distilling off the solvent, the amide intermediate obtained as the residue was dissolved in 4.5 ml of pyridine. 1.57 g of tosyl chloride was added thereto and the resulting mixture was stirred at 60° C. for 3 hours. The reaction mixture was then cooled to 5° C. and the precipitate thus formed was collected by filtration and washed with ethyl acetate. The organic layers were combined and aqueous solution of sodium chloride was added thereto. After adjusting to pH 2.0 with 6N HCl, the mixture was washed. The organic layer was dried over MgSO$_4$ and concentrated under reduced pressure. The resulting residue was purified by column chromatography with the use of 40 g of Wako Gel C-300. Fractions eluted with benzene/ethyl acetate (4:1 by volume) were combined and concentrated to thereby give 1.0 g of the nitrile compound 11.

Compound 11: NMR (CDCl$_3$) δppm: 1.42 (9H, s, t-Bu), 2.83 (1H, m, —CH$_2$—), 2.89 (1H, m, —CH$_2$—), 3.75 (3H, s, CH$_3$), 4.46 (1H, m), 5.13 (1H, broad d, —NH—), 5.41 (1H, dt, J=10.99, 1.32 Hz, =CH—CN), 6.46 (1H, ddd, J=10.99, 7.91, 7.25, —CH=CH—CN).

IR (KBr) νcm$^{-1}$; 2240, 1735, 1674.

65 mg of the compound 11 was dissolved in 0.5 ml of methylene chloride and 1 ml of 4N HCl adjusted with dioxane was added thereto under ice-cooling. After stirring the same temperature for 1 hour, the reaction mixture was concentrated under reduced pressure. The residue thus obtained was treated with ethyl ether and thus the compound 12 was obtained in the form of crystals.

Compound 12: NMR (D$_2$O) δppm: 3.08 (2H, m, —CH$_2$—), 3.86 (3H, s, CH$_3$), 4.41 (1H, t, J=6.37 Hz, —CH—CO$_2$), 5.77 (1H, dt, J=10.99, 1.32 Hz, =CH—CN), 6.68 (1H, dt, J=10.99, 7.69 Hz, —CH=CH—CN).

IR (KBr) νcm$^{-1}$: 2210, 1740.

The compound 12 was suspended in 1 ml of toluene and 0.4 ml of a 15% solution of trimethylaluminum in hexane was added thereto. After allowing the reaction mixture to react at room temperature for 16 hours, 2 ml of 1N HCl was added thereto under ice-cooling to thereby decompose the aluminum adduct and the excessive trimethylaluminum. After separating the aqueous layer, the organic layer was extracted again with 1N HCl. The aqueous layers were combined and conc. HCl was added thereto to adjust the HCl concentration to 3N. This solution was heated at 50° C. for 2.5 hours for hydrolysis of the ester. The reaction mixture was then concentrated to a small amount under reduced pressure and the residue was purified by column chromatography with the use of 10 ml of activated carbon. Then the column was washed with water and eluted with 30% methanol. Fractions containing the target compound were collected and concentrated to a small amount under reduced pressure, followed by freeze-drying. Thus 35 mg of the compound of the present invention (hydrochloride) represented by formula (I) wherein X was a nitrogen atom to which a hydrogen atom was bound and * was an (R), (S) mixture was obtained.

Compound of Example 4 [the compound of formula (I) wherein X is a nitrogen atom to which a hydrogen atom is bound while * is an (R), (S) mixture]:

NMR (D$_2$O) δppm: 2.65 (1H, m, —CH$_2$—), 2.73 (1H, m, —CH$_2$— ), 4.22 (1H, dd J=7.77, 6.11 Hz, —CH═CHC—NH), 6.01 (1H, ddd, J=9.98, 2.22, 1.6 Hz, ═CH—CN), 6.76 (1H, ddd, J=9.98, 4.71, 3.89 Hz, —CH═CH—CNH).

IR (KBr) νcm$^{-1}$: 1730, 1680.

UV λ$_{max}$=219 nm (ε8840).

EXAMPLE 5

The substance SF2698 which is the compound of the present invention represented by formula (I) wherein X is a nitrogen atom to which a hydrogen atom is bound and * is (S) may be chemically produced in the same manner as in Example 4 except for using the compound 9 whose configuration was (S), obtained in Examples 1 and 3 as a starting material.

Compound 11 (* =S): NMR (CDCl$_3$) δppm: 1.42 (9H, s, t-Bu), 2.83 (1H, m, —CH$_2$—), 2.89 (1H, m, —CH$_2$—), 3.75 (3H, s, CH$_3$), 4.46 (1H, m), 5.13 (1H, broad, d, —NH—), 5.41 (1H, dt, J=10.99, 1.32 Hz, ═CH—CN), 6.46 (1H, ddd, J=10.99, 7.91, 7.25, —CH═CH—CN).

IR (KBr) νcm$^{-1}$: 2240, 1735, 1674.

[α]$^{25}_D$=+108 (C 1.38, CHCl$_3$).

m.p.: 75°-77° C.

Compound 12 (*=S):

NMR (D$_2$O) δppm: 3.08 (2H, m, —CH$_2$—), 3.86 (3H, s, CH$_3$), 4.41 (1H, t, J=6.37 Hz, —CH—CO$_2$—), 5.77 (1H, dt, J=10.99, 1.32 Hz, ═CH—CN), 6.68 (1H, dt, J=10.99, 7.69 Hz, —CH═CH—CN).

IR (KBr) νcm$^{-1}$: 2210, 1740.

[α]$^{25}_D$=+32° (C 1.03, CH$_3$OH).

m.p.: 108°-110° C.

Substance SF2698 (hydrochloride): NMR (D$_2$O) δppm: 2.65 (1H, m, —CH$_2$—), 2.73 (1H, m, —CH$_2$— ), 4.22 (1H, dd J=7.77, 6.11 Hz, ═CHC—NH—), 6.01 (1H, ddd, J=9.98, 2.22, 1.67 Hz, ═CH—C—NH), 6.76 (1H, ddd, J=9.98, 4.71, 3.89 Hz, —CH═CH—C═NH).

IR (KBr) νcm$^{-1}$: 1730, 1680.

UV λ$_{max}$=219 nm (ε8840).

[α]$^{25}_D$=−26.7° (C 1.0, H$_2$O).

EXAMPLE 6

Figure 1A:
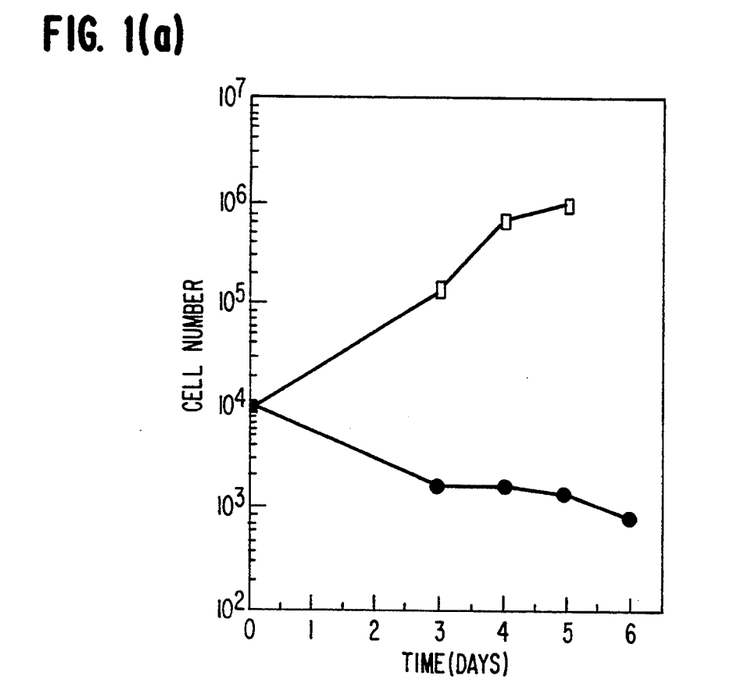
FIG. 1a shows the selective growth inhibition action of the compound of the invention on NIH3T3 cells transformed with the ras gene versus normal NIH3T3 cells in FIG. 1(b).
Figure 1B:
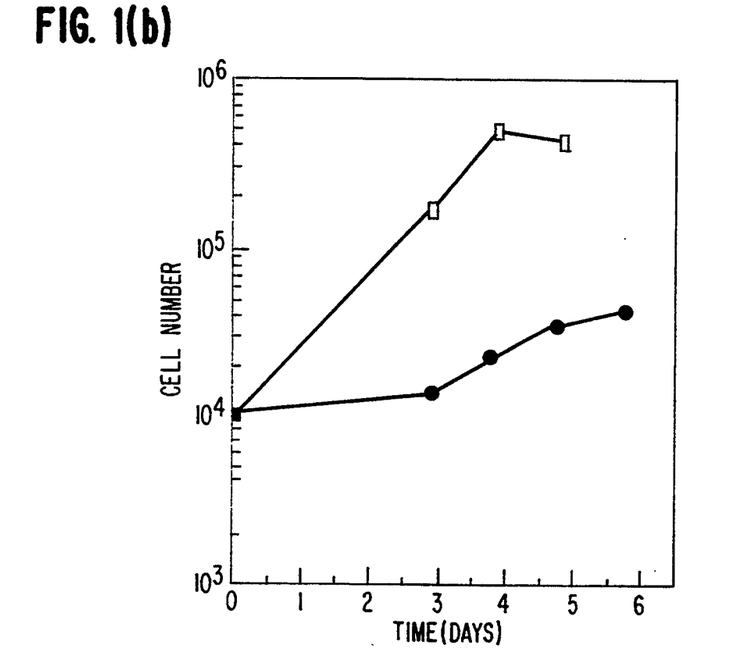

Specific growth inhibition by the compound of the invention on NIH3T3 cells transformed with activated c-Ha-ras gene NIH3T3 cells transformed with the activated ras gene (Proc. Natl. Acad. Sci. USA, 81, 4771-4775 (1984)) and normal NIH3T3 cells were incubated in a Dulbecco-modified Eagle medium containing 5% bovine serum. The initial cell concentrations were adjusted to 1×10$^4$ cells/ml. The compound obtained in Example 3 was added to a concentration of 40 μg/ml and the cell numbers were counted with the lapse of time from the 1st to the 6th days. FIG. 1 shows the results.

As FIG. 1 clearly shows, the compound inhibited the growth of the NIH3T3 cells transformed with the activated ras gene at a concentration of 40 μg/ml. In contrast, the normal NIH3T3 cells continued to grow at the same concentration.

EXAMPLE 7

Acquisition of revertant cells from transformed NIH3T3 cells with the compound of the invention NIH3T3 cells transformed with the activated c-Ha-ras gene and normal NIH3T3 cells were incubated for 6 days in the presence of 40 μg/ml of the compound obtained in Example 3 under the same conditions as in Example 6. The cells were microscopically observed in detail. As a result, the normal NIH3T3 cells showed no morphological change, while the transformed NIH3T3 cells partially died. The transformed NIH3T3 cells selectively surviving were revertants which were flat and had nuclei and nucleoli morphologically similar to the normal NIH3T3 cells.

To illustrate the properties of these revertants, the following Test Examples are provided.

TEST EXAMPLE 4

Expression of ras gene product p21 in revertant cells

The expression of the ras gene product p21 was examined in the revertant cells isolated in Example 7, NIH3T3 cells transformed with the ras gene and normal NIH3T3 cells in the following manner. 2×10$^6$ portions of these cells were collected and each suspended in 1 ml of a buffer solution (100 mM NaCl, 20 mM Tris hydrochloride (pH 7.5), 5 mM MgCl$_2$, 1% NonidetP-40 (polyoxyethylene(9)p-tert-octylphenol), 0.5% sodium deoxycholate, protease inhibitor) and then ground with a Potter homogenizer. After centrifuging at 3600 r.p.m. for 60 minutes, 10 μg portions of proteins were isolated from the supernatant by 12.5% polyacrylamide gel electrophoresis.

Figure 2:
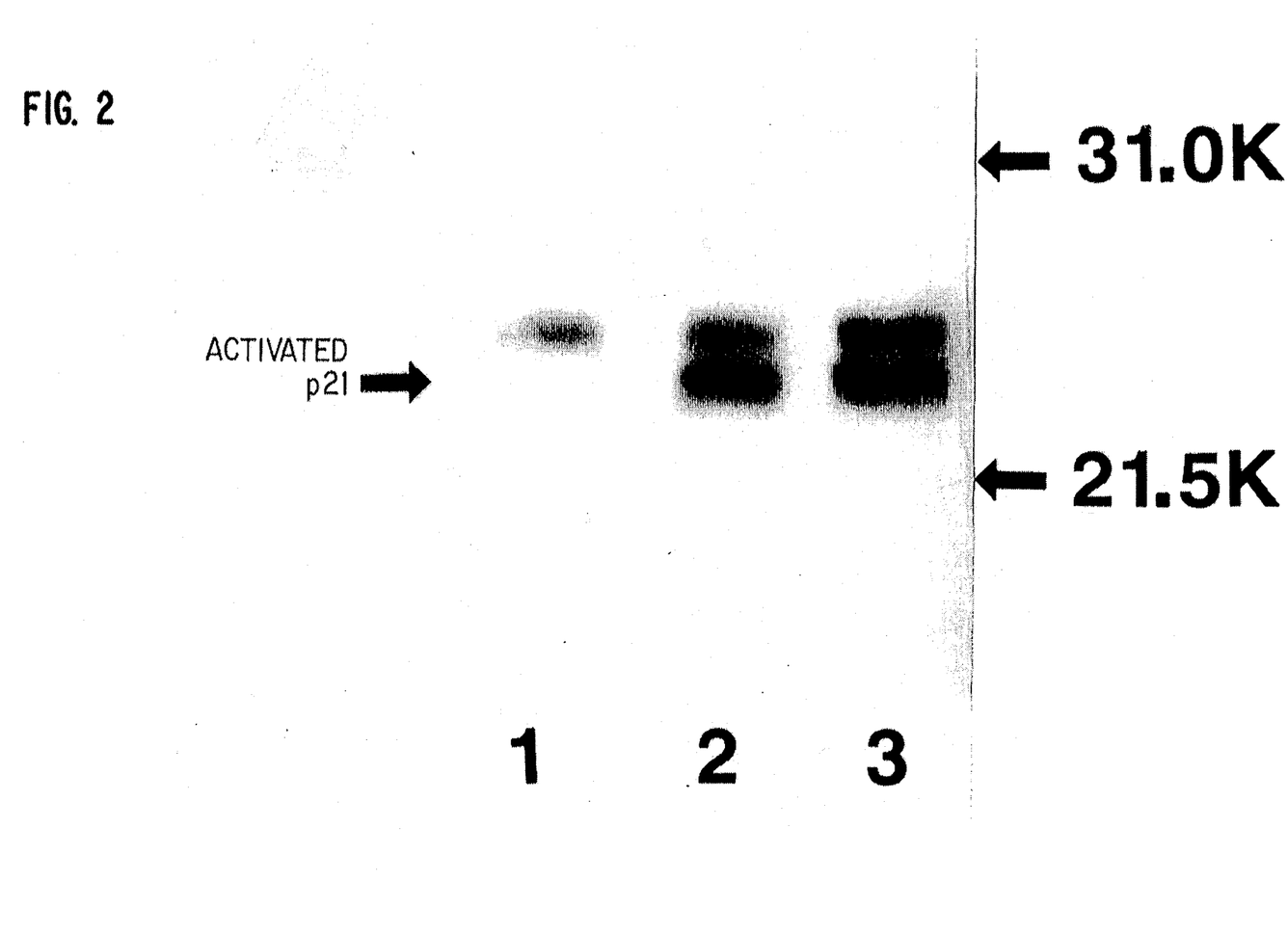
FIG. 2 shows the expression of the ras gene product p21 in revertants.

Then, the proteins in the gel were transferred into a nitrocellulose membrane and reacted with NCC-RAS-004, which was a monoclonal antibody for p21, at 4° C. for 24 hours to perform Western blotting. After reacting with rat Ig and $^{125}$I-Protein A, radioautography was performed. FIG. 2 shows the results. As FIG. 2 clearly shows, the activated p21 was expressed in the revertants as well as in the NIH3T3 cells transformed with the ras gene.

TEST EXAMPLE 4

Carcinogenic ability of revertant cells on nude mouse

3×10$^5$ portions of the revertant cells isolated in Example 7, NIH3T3 cells transformed with the ras gene and normal NIH3T3 cells were transplanted onto both shoulders of BALB/C nude mice aged 6 weeks. As a result, the transformed cells induced formation of tumors at doses of 3×10$^5$ cells and 3×10$^4$ cells, while the revertants scarcely induced tumor formation even at a dose of 3×10$^5$.

According to the present invention, an excellent oncogene suppressor and an excellent revertant cell-obtaining agent can be provided.

What is claimed is:

1. A compound represented by formula (I):

wherein X represents an oxygen atom or a sulfur atom; or a pharmaceutically acceptable salt said compound.

2. A compound as claimed in claim 1, wherein the configuration of the carbon atom binding to the carboxyl group is (S), (R) or a mixture of (S) and (R).

3. The compound as claimed in claim 1, wherein X is an oxygen atom.

4. The compound as claimed in claim 1, wherein X is a sulfur atom.

5. The compound as claimed in claim 2, wherein said configuration is (S).

6. The compound as claimed in claim 2, wherein said configuration is (R).

7. The compound as claimed in claim 2, wherein said configuration is a mixture of (S) and (R).

* * * * *